United States Patent
Beerwerth et al.

(10) Patent No.: US 11,285,336 B2
(45) Date of Patent: Mar. 29, 2022

(54) LIGHT-BASED EPILATION DEVICE AND METHOD OF COSMETIC HAIR REMOVAL

(71) Applicant: Braun GmbH, Kronberg (DE)

(72) Inventors: Frank Beerwerth, Kaltenholzhausen (DE); Uwe Bielfeldt, Bad Soden (DE); Dalibor Dadic, Koenigstein (DE); Felix Heinemann, Frankfurt am Main (DE)

(73) Assignee: Braun GMBH, Kronberg (DE)

( * ) Notice: Subject to any disclaimer, the term of this patent is extended or adjusted under 35 U.S.C. 154(b) by 239 days.

(21) Appl. No.: 16/038,781

(22) Filed: Jul. 18, 2018

(65) Prior Publication Data

US 2019/0038913 A1    Feb. 7, 2019

(30) Foreign Application Priority Data

Aug. 1, 2017 (EP) .................................... 17184316
Jun. 28, 2018 (EP) .................................... 18180381

(51) Int. Cl.
*A61N 5/06* (2006.01)
*A61B 18/00* (2006.01)

(52) U.S. Cl.
CPC .. *A61N 5/0617* (2013.01); *A61B 2018/00476* (2013.01); *A61N 2005/0629* (2013.01); *A61N 2005/0644* (2013.01); *A61N 2005/0651* (2013.01); *A61N 2005/0652* (2013.01)

(58) Field of Classification Search
None
See application file for complete search history.

(56) References Cited

U.S. PATENT DOCUMENTS

| | | | |
|---|---|---|---|
| 6,217,572 B1 | 4/2001 | Tobinick | |
| 6,666,878 B2 | 12/2003 | Carlgren | |
| 6,860,896 B2 | 3/2005 | Leber et al. | |
| 9,737,727 B2 | 8/2017 | Unger | |
| 2002/0188334 A1 | 12/2002 | Carlgren | |
| 2004/0044384 A1 | 3/2004 | Leber et al. | |
| 2007/0038206 A1* | 2/2007 | Altshuler | A61B 18/203 606/20 |
| 2009/0287195 A1 | 11/2009 | Altshuler et al. | |
| 2012/0116373 A1* | 5/2012 | Moench | A61B 18/203 606/9 |

(Continued)

FOREIGN PATENT DOCUMENTS

| | | |
|---|---|---|
| CN | 1901968 A | 1/2007 |
| CN | 106535804 A | 3/2017 |

(Continued)

OTHER PUBLICATIONS

European search report dated Dec. 8, 2017.

(Continued)

*Primary Examiner* — Erica S Lee
(74) *Attorney, Agent, or Firm* — StefanMichael Schneider; Kevin C. Johnson

(57) ABSTRACT

A light-based epilation device having at least two sub-groups of light emission elements, each of the sub-groups of light emission elements having at least one distinct light emission element, wherein the sub-groups of light emission elements are arranged for separate energizing, and a controller unit arranged for energizing the sub-groups of light emission elements in accordance with an energizing sequence so that the light emission unit quasi-continuously emits light

3 Claims, 2 Drawing Sheets

(56) References Cited

U.S. PATENT DOCUMENTS

| | | |
|---|---|---|
| 2013/0227841 A1 | 9/2013 | Solomon et al. |
| 2014/0094879 A1 | 4/2014 | Van Os et al. |
| 2015/0224339 A1 | 8/2015 | Unger |
| 2015/0230863 A1* | 8/2015 | Youngquist .......... A61B 5/4833 606/9 |
| 2016/0287333 A1* | 10/2016 | Morrison ............. A61B 18/203 |
| 2016/0310212 A1 | 10/2016 | Domankevitz |
| 2017/0172660 A1 | 6/2017 | Mehl et al. |

FOREIGN PATENT DOCUMENTS

| | | |
|---|---|---|
| GB | 2526764 A | 12/2015 |
| WO | 2012172456 A2 | 12/2012 |
| WO | 2014076503 A1 | 5/2014 |

OTHER PUBLICATIONS

European search reports dated Oct. 30, 2018, and Jan. 1, 2020.
International Search Report and Written Opinion; Application Ser. No. PCT/IB2018/055309; dated Oct. 30, 2018; 10 pages.
First Search dated Jan. 16, 2021; Chinese Application No. 2018800504349; China National Intellectual Property Administration.

\* cited by examiner

LIGHT-BASED EPILATION DEVICE AND METHOD OF COSMETIC HAIR REMOVAL

FIELD OF THE INVENTION

The present disclosure is concerned with a light-based epilation device for at least temporal hair removal comprising an array of light emission elements.

BACKGROUND OF THE INVENTION

It is generally known that skin can be treated with light to obtain various effects ranging from cosmetic treatments to medical treatments. In particular for cosmetic hair growth manipulation or hair growth management, many devices can be bought by consumers for unsupervised home use, which devices use a repeatedly flashing flash lamp—so called intense pulsed light (IPL) devices. Some manufacturers recommend not to use such a device in case the user suffers from epilepsy as it is believed that the strong light pulses might cause epileptic seizure. Other manufacturers recommend not looking at the skin and device during treatment, but this is not practical, as the consumer wants to see the treatment area.

Hence there is a need to provide a light-based epilation device that is improved over the known devices, in particular in which care is taken to reduce the risk of epileptic seizure or to reduce a general discomfort a user might experience when using such a device.

SUMMARY OF THE INVENTION

In accordance with at least one aspect a light-based epilation device for at least temporal hair removal having a light emission unit having an array of light emission elements, in particular semiconductor light emitter elements such as LEDs, having at least two sub-groups of light emission elements, each of the sub-groups of light emission elements having at least one distinct light emission element, wherein the sub-groups of light emission elements are arranged for separate energizing, and a controller unit arranged for energizing the sub-groups of light emission elements in accordance with an energizing sequence so that the light emission unit quasi-continuously emits light, the energizing sequence having consecutive sub-sequences that each have each of the sub-groups of light emission elements at least once and where at least one sub-group is not energized at any given time instant, and where the energizing sequence has at least one non-energizing gap having a length so that the non-energizing gap is not noticed by a human observer, in particular where the non-energizing gap is in the range of between 1 µs and 4000 µs.

In accordance with at least one aspect, the present disclosure is also concerned with a method of cosmetic hair growth manipulation, comprising the steps of providing a light-based epilation device as proposed in the previous paragraph, bringing a light output window of the light-based epilation device into contact with the skin of a human subject, moving the light output window over the skin while maintaining skin contact and controlling the light-based epilation device to quasi-continuously emit light, and providing at least one non-energizing gap in the light emission, which non-energizing gap has a length such that a human observer does not note the interruption of the light emission, in particular has a length in a range of between 1 µs and 4000 µs.

BRIEF DESCRIPTION OF THE DRAWINGS

The present description will be further elucidated by a detailed description of example embodiments, where reference is made to figures. In the figures

DETAILED DESCRIPTION OF THE INVENTION

Figure 1:
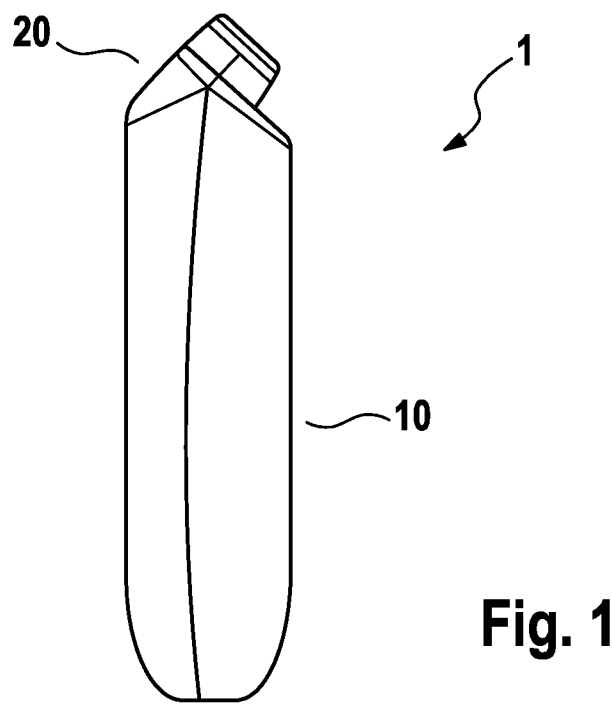
FIG. 1 is a schematic side view depiction of an example light-based epilation device.

The term "quasi-continuous" with respect to light emission is herein defined to mean a light emission sequence that is recognized as being uninterrupted by an average human observer. It is well known that the human eye cannot, e.g., recognize the flicker introduced by the dark phases of a standard film projection provided with a 48 or 50 Hz rate. This is generally referred to as the flicker fusion rate or flicker fusion threshold (the flicker fusion threshold depends on many parameters, but based on experience, the flicker in old-fashioned film projection is typically not noted by a human observer). This might be due to the persistence of vision, which means that a bright spot is still "seen" by a human eye for a short period after it is switched off. In order to avoid that the human eye detects a switch-off of a light emission, the switch-off period should be substantially shorter than the 20 ms of the single image presentation of a 50 Hz sequence, e.g. applying a factor of 5 leads to switch-off periods of 4 ms, which was identified in investigations as a switch-off length that is not recognized by the human eye as being an interrupted light emission for light-based epilation devices. An emission sequence having one or several, in particular periodically appearing non-energizing gaps (where no light is emitted) of 4 ms or below (e.g. the temporal length of the non-energizing gap may be in a range of between 1 µs and 4000 µs) will be recognized as being continuous by a statistically relevant portion of humans for typical light intensities emitted by a light emission unit used for at least temporal hair removal in a light-based epilation device. As the light emission is in fact not continuous, but interrupted in a manner that a human does not note the interruption, the term "quasi-continuous" is used to reflect this, i.e. "quasi-continuous" means here a continuous light emission having at least one or several, in particular periodically occurring non-energizing gaps (i.e. dark phases) that have a length that the interruption of the light emission is not noted by a human observer, in particular where the temporal length of the non-energizing gap is below 4 ms, in particular is in the range of between 1 µs and 4000 µs.

While the length of the non-energizing gaps may depend on various factors to be not observable by a human (such as light intensity, wavelength, fatigue of the human etc.) and needs in particular to accommodate a measurement to be performed during the non-energizing gap such as the measurement of a skin characteristic using optical measurement principles, the length of the non-energizing gaps may lie in the range of between 1 µs and 100 µs, between 10 µs and 500 µs, between 50 µs and 200 µs, between 1 ms and 2 ms, between 10 µs and 1 ms etc.

The term "array" as used herein shall mean a non-limited arrangement of a plurality of light emission elements, where a light emission element might be a light emitter element such as an LED die. That means the light emitting elements may be arranged in an irregular pattern, even though a regular pattern such as an array having rows and columns may be easier to manufacture. Hence, regular patterns are as well contemplated, e.g. the location distribution may have a rows and columns structure. The size of the array is given by the active (i.e. light emitting) area it covers, where the active area of the array of light emission elements of the light emission unit may have a regular form such as a rectangle, a triangle, a regular polygon, or a circle, an ellipse or an oval. The size of the active area covered by the array is generally arbitrary, e.g. it may lie in a range of between 1 mm$^2$ and 10.000 mm$^2$, but for a light-based epilation device, the size of the active area may be in a range of between 25 mm$^2$ and 1000 mm$^2$, in particular in a range of between 60 mm$^2$ and 500 mm$^2$.

The term "light emission element" shall refer to an individually controllable light source, in particular to small sized light sources such as semiconductor light emitters, e.g. VCSELs or LEDs or OLEDs. Two examples of such light emitting elements are the DURIS® P 9 GW PUSTA1.PM white emitting high power LED and the OSLON® SSL 80 GH CS8PM1.24 high performance LED emitting at 660 nm, both LEDs being available from Osram Opto Semiconductors GmbH, Regensburg, Germany But these two examples are non-limiting, in particular with respect to the performance, and other light emitters are suitable as well, where the skilled person will easily choose a fitting light emitter from the list of available products for a given application. Where an LED is mentioned, this may refer to a packaged LED or an LED die that can be mounted on a substrate at a high density to provide high intensity light as needed for e.g. hair growth manipulation.

The light emission unit as proposed herein comprises a plurality of sub-groups of light emission elements, where the light emission element(s) of one sub-group are not overlapping with any other sub-group, i.e. each light emission element is only assigned to one single sub-group. The light emission unit further is coupled with a controller that is arranged to energize the sub-groups of light emission elements in accordance with an energizing sequence so that the light emission unit quasi-continuously emits light in a manner that a human user is essentially not noticing any interruptions in the light emission (above a definition was provided to explain the herein used term "quasi-continuous light emission"). The energizing sequence varies the energizing of the sub-groups over time so that at each time instant at least one of the sub-groups is energized and at least one other of the sub-groups is not energized, in particular at least 50% or at least 67% of the sub-groups of light emission elements are not energized at any given time instant of applying the energizing sequence. This may ease the heat management of the device on the one hand and the powering requirements on the other hand. Each sub-group of light emission elements comprises at least one light emission element, even though a sub-group of light emission elements may comprise two, three, four, five, six, seven, eight, nine, ten, twelve, fifteen, twenty etc. light emission elements. While this is optional, in some embodiments, each sub-group of light emission elements has the same number of light emission elements. The light emission elements may be arranged in regular rows and columns, e.g. a 15 times 5 array of 45 light emission elements is considered as well as an 8 times 27 array of 216 light emission elements etc. Essentially, the array of light emission elements may have two and any larger number of light emission elements so that each sub-group of light emission elements has one or any higher number of light emission elements. The light emission elements of the sub-groups may be arranged as well in rows and columns E.g. in a 4 times 24 array, two sub-groups of 4 times 12 light emission elements may be consecutively arranged or four sub-groups of 2 times 12 light emission elements may be arranged in a 2 by 2 matrix. In a 4 times 24 array, the center 2 times 16 light emission elements may constitute a first sub-group of 32 light emission elements and the outer rectangular "ring" of 64 light emission elements may then form a second sub-group. The sub-groups of light emission elements may generally be arranged as a regular M times N matrix, where M and N are integer numbers of any value. In another example, of a 6 times 9 array, every other light emission element in the matrix is forming one sub-group and the remaining light emission elements form the other sub-group, which means that in some embodiments, a sub-group of light emission element can spatially overlap with at least one other sub-group.

In some embodiments, the light emission is kept relatively constant, where the variation in light power emitted by the light emission unit in a sliding 40 ms window is at or below 20% (i.e. ±10%). A high constancy of the light emission supports the recognition of the light emission as being continuous.

In some embodiments, the controller is arranged to energize more than one sub-group of light emitting elements during a given time period, i.e. the applied energizing sequence is not necessarily restricted to a consecutive energizing of the sub-groups but may comprise parallel energizing of at least two sub-groups, where always at least one of the sub-groups of light emission elements is not energized. Due to the finite number of sub-groups of light emission elements of a light emission unit, the energizing sequence comprises sub-sequences that may in particular be repetitions of the same basic sequence. E.g. a light emission unit may comprise two subgroups A and B and the basic sequence may then be: A(30 ms)-B(30 ms), where the 30 ms in brackets means the time period the respective sub-group is energized before the next sub-group is energized. The energizing sequence may then be A(30 ms)-B(30 ms)-A(30 ms)-B(30 ms), where the repeating basic sequence forms the sub-sequences of the energizing sequence.

The energizing sequence is defined to continue ad infinitum, but the controller is arranged to apply the energizing sequence to provide a continuous light emission within a controlled time period, which means that the controller applies the sequence after the controller has received a start signal and continues until the controller receives a stop signal. A start and stop signal may e.g. be generated by an ON/OFF switch. If used in a light-based epilation device, a start signal may automatically be generated once skin contact of a light output window is established and a stop signal may automatically be provided when the light output window loses skin contact or a start/stop signal may be generated in connection with the detection of a motion of the light output window over the skin. The light-based epilation device may generate an OFF signal in case the device overheats.

A light-based epilation device is proposed in which a light emission unit and a controller as disclosed are provided. The light-based epilation device may in particular have a handle section intended for being held by a user's hand and a head section intended for providing the skin treatment in form of emitted light. As was discussed before, a quasi-continuous light emission (i.e. an emission of light that is recognized by a human's eye as essentially being continuous) will be provided by the device. The light-based epilation device may be intended for mere cosmetic applications or for medical treatments (e.g. prophylactic therapeutic applications or treatment of pathological conditions).

As has already been mentioned, the use of a known IPL device applying individual high intensity light flashes may cause an epileptic seizure. But individuals that do not suffer from epilepsy have reported that they consider the strong light flashes as unpleasant. A light emission unit as described herein is arranged to "quasi-continuously" emit light and thus is arranged to provide the same effects as flash-lights, but with a higher acceptance by users and with a reduced potential to cause epileptic seizure due to the avoidance of recognizable flashing.

Instead of continuously energizing a single light source or continuously energizing an array of light sources, the herein disclosed light emission unit comprises a plurality of sub-groups of light emitting elements and at least one sub-group is always not energized. This allows to better deal with heat management of the device. As was explained, the light-based epilation device always energizes an array area having a minimum size, e.g. at least 25 $mm^2$.

The light-based epilation device may be controlled in a manner that a spot on the skin receives a certain minimum light fluence (e.g. 2 $J/cm^2$, an upper light fluence of 10 $J/mm^2$ may be considered), in particular within a given time window (e.g. the time window may lie in the range of between 30 ms to 200 ms for the here considered hair growth manipulation applications). The area of the light emission unit that emits light at a given time instant may be chosen to have a certain minimum area, which may be in the range of between 20 $mm^2$ to 500 $mm^2$, in particular in the range of between 25 $mm^2$ to 200 $mm^2$. In some embodiments, the active area is at least 64 $mm^2$. The illuminating area may in particular be a connected area and the area may comprise a circle having a diameter of at least 5 mm, in particular of at least 8 mm (i.e. the connected area should not be arbitrarily small in one of the dimensions in which it extends, e.g. should be rather 5 mm times 5 mm than 1 mm times 25 mm. In one way to describe such a light-based epilation device, one may say that the light submission unit continuously provides light pulses that illuminate the skin to provide a skin treatment effect, which light pulse are consecutively provided from different sub-areas of the active area of the array of light emission elements. The light intensity is chosen to be relatively low so that the pulses of e.g. 30 ms to 200 ms length are much longer than the usual flash lamp light pulses of a few milliseconds. In this way, a quasi-continuous light emission is generated that still provides the intended skin treatment benefit but also eases user comfort and reduces risk of epileptic seizures.

In a light-based epilation device as proposed, the controller may be arranged to provide regular or irregular non-energizing gaps in the light emission (i.e. periods in which no light is emitted), which non-energizing gaps are so short that the human eye would essentially not notice the interruption. The interruption may be used to measure a skin parameter by a sensor unit comprising a light source for illuminating the skin and a light sensor for measuring the light that is reflected or scattered back from the illuminated skin. The controller may be arranged to use the measured skin parameter to modify or adapt the energizing sequence, e.g. to increase or decrease a time period of energizing one or more sub-groups of light emission elements and/or of increasing or decreasing a current to the energized light emission elements in order to increase or decrease the light intensity. As mentioned before, the controller may be arranged to start and stop the quasi-continuous light emission when a skin contact of a light output window is established or ceases.

It may be contemplated that a sensor for measuring a skin parameter is used that is not influenced by the intense light emitted by the light emission elements, e.g. sensors that are sensitive to light at a wavelength remote from the wavelength that is used for the treatment. An internal sensor allows to measure the skin parameter at a high frequency (e.g. with 10 Hz) and thus allows to automatically adapt to localized skin parameter variations.

The present disclosure is also concerned with a method of cosmetic hair growth manipulation. Hair growth manipulation done for mere aesthetical reasons is considered a cosmetic method, while hair growth reduction done in the presence of excessive hair growth (hirsutism or hypertrichosis) is considered a non-cosmetic method. The cosmetic hair growth manipulation method then comprises using a light-based epilation device as proposed herein, bringing a light output window into skin contact, and applying a quasi-continuous light beam onto the skin, in particular where this step includes moving the light output window across the skin. This latter step involves providing at least one energizing gap having a length of 4 ms or below, in particular for measurement of a skin parameter and/or measurement of a speed of the movement of the skin output window over the skin and in particular controlling at least one parameter of an applied energizing sequence in dependence on the measured skin parameter and/or speed.

In some examples, the sub-groups of light emission elements are consecutively arranged along a longer elongation direction of an oblong array of light emission elements and the controller is arranged to energize the sub-groups consecutively from one end of the oblong array to the other end. The cosmetic hair growth manipulation method may then involve moving of the light output window in a direction perpendicular to the longer elongation direction along which the sub-groups are consecutively arranged, measuring of a speed of the light output window over skin, and of controlling the energizing sequence such that the skin areas illuminated by each sub-group are essentially arranged gap-free, i.e. the energizing sequence has a timing that is coordinated with the speed of the device so that the illumination of the next skin area by a given sub-group of light emission elements occurs when the light output window was completely moved over the previously illuminated skin area and the illumination starts (or slightly overlaps) with the edge of the previous illumination area.

Figure 2:
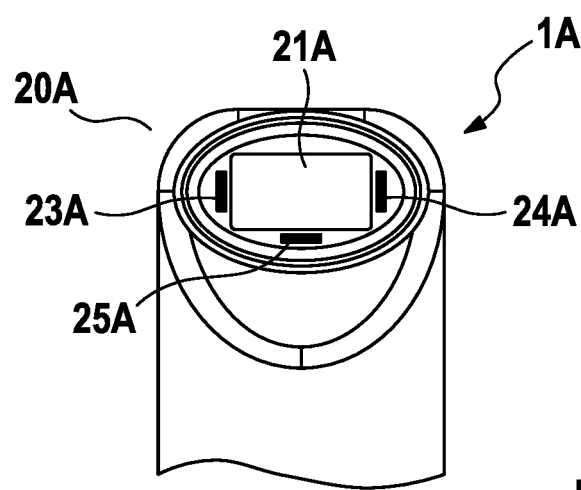
FIG. 2 is a schematic front view onto an example head section of a light-based epilation device.

FIG. 1 shows a side view onto an example light-based epilation device 1 that has a handle section 10 and a head section 20. FIG. 2 shows a front view onto a top portion of an example light-based epilation device 1A having a head section 20A in which a light output window 21A is embedded. A light emission unit may be disposed just close to the level of the light output window defined by the surrounding head section housing 22A. The light output window 21A may comprise a shield that is essentially transparent for the treatment light and protects the light emission unit from becoming soiled, but this is an optional feature. It is schematically shown that in the depicted embodiment some sensors 23A, 24A, and 25A are disposed in the head section 20A close to the light output window 21A; in another example one or more sensors may alternatively or additionally also be disposed in the area of the light output window. These are optional features and the number of three sensors is just an example. Sensors 23A and 24A may be sensors adapted to measure a skin parameter such as skin color and/or hair color. Sensor 25A may be a sensor that is adapted to measure the speed of the device with respect to the skin and/or the skin contact. Such a sensor may be realized as a photodiode array sensor as is known from an optical mouse.

Figure 3:
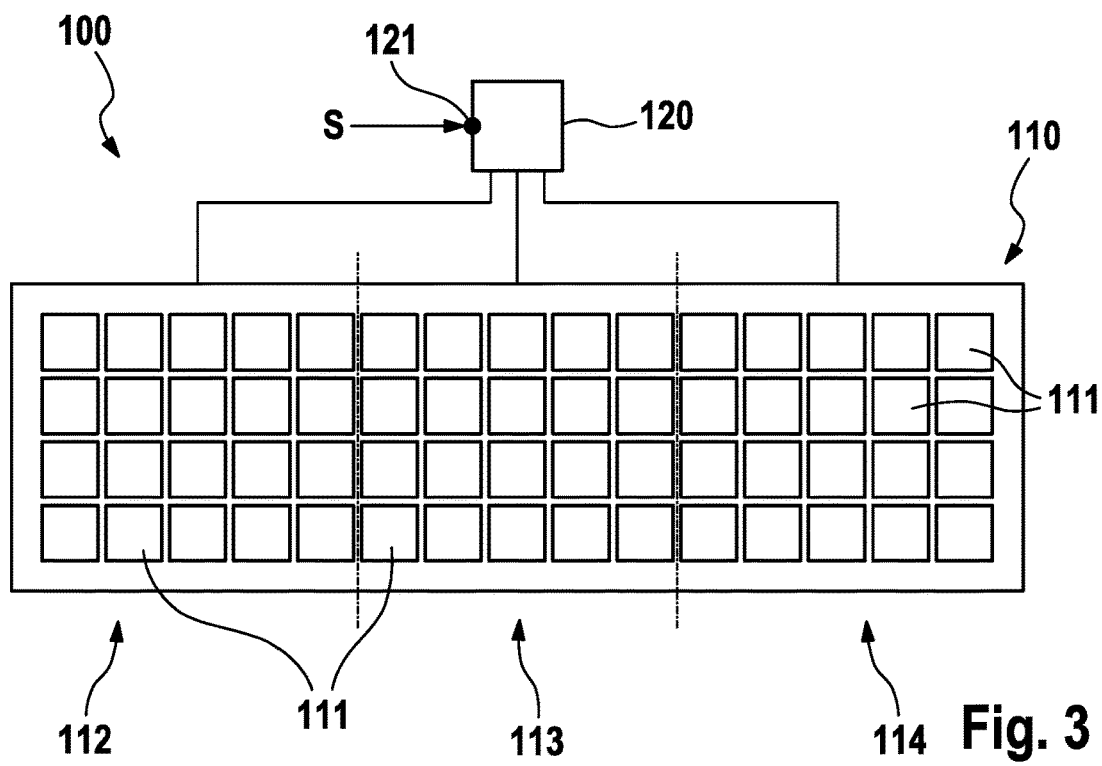
FIG. 3 is a schematic depiction of an example light emission unit comprising three sub-groups of light emission elements.

FIG. 3 is a schematic depiction of a light emission unit 100 having an array of light emission elements 110, which array 110 comprises in the shown embodiment a regular rectangular arrangement of 15 columns having each four light emission elements 111 (i.e. a 4 times 15 array). The light emission unit 100 comprises a controller 120 that is coupled with the array of light emission elements 110 for selective energizing of sub-groups of light emission elements 112, 113, and 114. The controller 120 is coupled with the array 110 in a manner to selectively and independently energize each of the three sub-groups of light emitting elements 112, 113, and 114. In FIG. 3 the sub-groups of light emitting elements are separated by dashed lines for sake of comprehensibility. Each of the sub-groups 112, 113, and 114 comprises a four times five arrangement of light emission elements 111. Each of the light emission elements 111 is assigned to only one sub-group. The controller has an input 121 for receiving a control signal S, e.g. a start signal or a stop signal. E.g. the input 121 may be coupled with an ON/OFF switch.

The shown 4 times 15 array is one example of an oblong array of light emission elements. The longer elongation direction extends from the left end of the array to the right end of the array (left and right are used with respect to the depiction of the array on the printed paper). The here three sub-groups of light emission elements 112, 113, and 114 are arranged consecutively in the longer elongation direction.

In one example, the controller 120 is arranged to energize (in response to a start signal) the first sub-group of light emission elements 112 for a first time period and to then energize the second sub-group of light emission elements 113 for a second time period essentially instantaneously after the end of the first time period and to then energize the third sub-group of light emission elements 113 for a third time period essentially instantaneously after the end of the second time period. The controller 120 may in particular be arranged to then repeat this sub-sequence of energizing the sub-groups of light emission elements 112, 113, and 114 until a stop signal is received by the controller 120. In this example, about 67% of the active area of the array of light emission elements is not energized when applying the energizing sequence. It is generally contemplated that the light emission unit 100 provides a quasi-continuous light emission between the start signal and the stop signal. As was explained, this requires that any non-energizing gap between the energizing time periods is below about 4 ms so that the human eye cannot recognize the "black" phase in between the intense light emission periods.

In some embodiments, the controller is arranged to provide interruptions in the energizing of the sub-groups of light emission elements in a regular or even periodic manner, e.g. the controller may be arranged to provide a 4 ms, 3 ms, 2 ms or 1 ms non-energizing gap (where light emission is interrupted) at a rate of 50 Hz (i.e. every 20 ms). This means that an, e.g., 30 ms light pulse will then be interrupted for the time of the non-energizing gap. As is known from film projection, the usual human subject will not note a short black phase (similar to the black phases of film projection caused by a changeover shutter between the movements of the film to the next picture) that occurs at a high frequency. While it is believed that a short non-energizing gap of 4 ms or below will not be recognized by the human user if it occurs relatively seldom (e.g. in a range of between 1 to 10 Hz) due to the pertinence of the perception of the human eye, a regularly occurring non-energizing gaps occurring at e.g. 50 Hz may provide another measure to make the quasi-continuous light emission to be recognized as being continuous. Of course, the regular non-energizing gaps may occur at other frequencies, e.g. at 40 Hz, 45 Hz, 55 Hz, 60 Hz, 65 Hz, 70 Hz, 75 Hz, 80 Hz, 85 Hz, 90 Hz, 95 Hz, 100 Hz etc. and the length of the non-energizing gap may have a shorter length than 4 ms, e.g. the length of the non-energizing gap may be 3 ms or 2 ms or 1 ms or 0.5 ms or 0.25 ms or 0.1 ms or 0.01 ms or 0.001 ms. In case that a measurement should happen during a non-energizing gap (e.g. the measurement of a skin characteristic or skin parameter using a photodiode), the length of the non-energizing gap can be adapted to, e.g., a dead-phase of a used photodiode caused by the intense light reflected back onto the active area of the photodiode.

Figure 4:
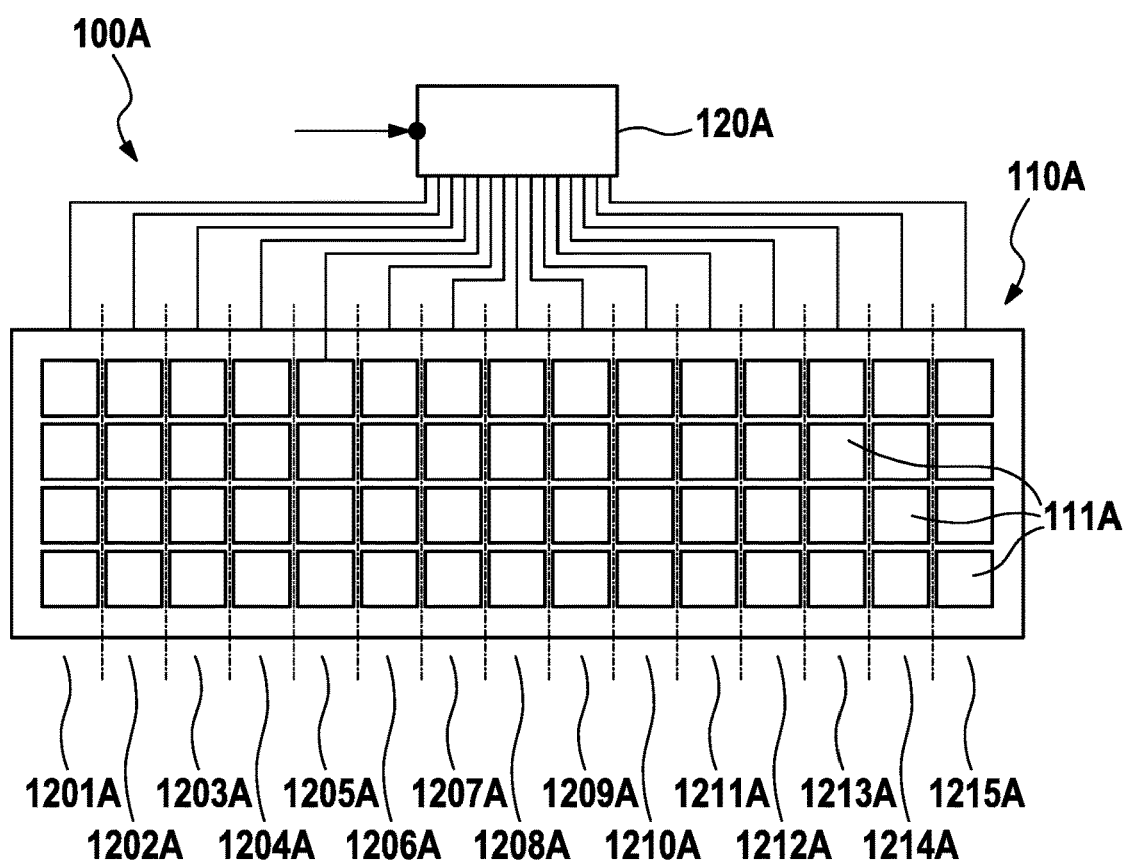
FIG. 4 is a schematic depiction of another example light emission module comprising fifteen sub-groups of light emission elements.

FIG. 4 shows another embodiment of a light emission unit 100A having an array of light emission elements 110A and a controller 120A coupled with the array 110A for selective and independent energizing of 15 sub-groups of light emission elements 1201A to 1215A, where each sub-group of light emission elements 1201A to 1215A has four light emission elements 111A arranged in a column. In FIG. 4, the sub-groups 1201A to 1215A are again separated by dashed lines. The array 110A is again shown as a regular arrangement of 15 times four light emission elements 111A. This was just chosen as an example and it is understood that essentially any arbitrary arrangement of light emission elements can be utilized. The finer partitioning of the array 110A into sub-groups allows a finer graded control of the energizing of the sub-groups. As will be explained below with respect to using a proposed light emission unit 100A in a light-based epilation device, it may be sensible to energize as many light emission elements 111A at once so that always a minimum area of the light emission unit 100A emits light, which minimum area may be 25 mm$^2$ or above. Assuming that each light emission element 111A covers an area of 1.25 mm$^2$ (which is only an example and is not to be construed as limiting), simultaneous energizing of five adjacent sub-groups of light emission elements (e.g. sub-groups 1201A to 1205A) would lead to a light emitting active area of 25 mm$^2$. The energizing sequence to be applied by the controller 120A may now be set in contrast to the sequence that was discussed with respect to FIG. 3. In FIG. 3, it was stated that the energizing sequence is 1-2-3-1-2-3-1-2-3- . . . , where 1, 2, and 3 refer to the sub-groups. Now, in the example of FIG. 4, fifteen sub-groups 1 to 15 are present and the sequence may start with the simultaneous energizing of sub-groups 1 to 5 as is indicated in FIG. 4 by a respective shading of the respective light emitting elements (in FIG. 4 referenced as 1201A to 1205A). Simultaneous energizing is indicated by the number of the sub-groups in square brackets: [1-2-3-4-5]. The energizing sequence may now comprise that in every new sequence step, the first sub-group (here sub-group 1 meaning 1201A) is de-energized and the next sub-group adjacent to the last sub-group (here sub-group 5 meaning 1205A is the last sub-group of the first sequence step and sub-group 6 meaning 1206A is then the next adjacent sub-group). The resulting sequence then reads [1-2-3-4-5] (10 ms)-[2-3-4-5-6](10 ms)-[3-4-5-6-7](10 ms)-[4-5-6-7-8] (10 ms), where again the energizing time period is given in brackets, where the here given 10 ms are to be considered as a non-limiting example. One may say that an emission window of 5 mm width slides across the light emission module. In some embodiments, the sequence continues at the end of the light emission unit 100A as follows: [11-12-13-14-15]-[1-12-13-14-15]-[1-2-13-14-15]-[1-2-3-14-15]-[1-2-3-4-15]-[1-2-3-4-5]-[2-3-4-5-6], where here the energizing time period was omitted for sake of simplicity. In this sequence list, the fifth sequence entry is the start of the repetition of the complete sub-sequence that starts with [1-2-3-4-5] and ends with [1-2-3-4-15]. The in principle never ending energizing sequence (which may only be stopped in case the controller receives a stop signal) then comprises consecutive sub-sequences that each have 15 sub-sequence steps. Where the energizing time period of the first sub-group 111 of FIG. 3 may be, e.g., 30 ms, the energizing time period for each sub-sequence step with reference to FIG. 4 may then be 6 ms, which leads to the same total energizing time period per sub-sequence as in FIG. 3, namely 90 ms. A non-energizing gap may be provided at least once per energizing sequence or in particular at least once per sub-sequence or may be provided after every fifth sequence entry or even after every sequence entry or a non-energizing gap may be provided, e.g., just every 25 ms so that a currently ongoing sequence entry is interrupted for the non-energizing gap and then the ongoing sequence entry is continued. The latter approach allows providing the non-energizing gap at a preferred frequency that is independent from the length of a single sequence entry etc.

Any light emission unit described here may be used in a light-based epilation device as schematically shown in FIGS. 1 and 2. Various hair treatments can be contemplated over a certain range of light emission wavelengths, pulse lengths, fluences on the skin etc. Hair treatment (i.e. hair growth management) by light may be merely cosmetic (e.g. just for controlling/managing hair growth for aesthetic reasons) or may be for prophylactic therapy or for medical reasons (e.g. treatment of hirsutism).

In the following, parameters are discussed that are suitable for cosmetic hair growth manipulation (hair growth manipulation may include hair growth enhancement and/or hair growth reduction). As is generally known, light will be absorbed, inter alia, by the melanin in the skin, which melanin is concentrated in the hair follicles and, depending on the pigmentation level, is present in the skin. Light absorption in the melanin causes heating of the melanin particles and thus of the tissue surrounding the melanin. If the right temperature is achieved over a sufficient tissue volume of the hair follicle, then the protein coagulation/denaturation that occurs essentially stops hair growth and the hair will eventually fall out (which relates to hair growth reduction as one form of hair growth manipulation). Light wavelength suitable for hair growth management lies in the range of between 600 nm and 1100 nm, in particular in the range of between 650 nm and 1000 nm, where the absorption of light by water or hemoglobin is much lower than the absorption of light in melanin so that the heating of other tissue is kept low. The lower the wavelength, the higher is the absorption of light in melanin, such that light in the visible range (i.e. 600 nm to 700 nm) is preferred due to the higher absorption coefficient. As was described already, the light emission unit as proposed sequentially energizes sub-groups of light emitting elements of an array of light emission elements. This leads to a pulse-like illumination of skin areas. The fluence per skin area and pulse should be above 2 $J/cm^2$ in order to achieve a sensible effect for hair growth manipulation (even though 1 $J/cm^2$ may be sufficient under certain circumstances). For a home use device, the fluence is typically not chosen to raise above 10 $J/cm^2$ and a fluence in the range of between 2 $J/cm^2$ and 7 $J/cm^2$ is considered as sensible. A typical pulse length of the skin irradiation lies in a range of between 30 ms and 200 ms, where in particular higher pulse length (at given fluence on the skin) may not be able to achieve the necessary temperature in the hair follicle due to heat dissipation.

The light emitted by the light emission unit for treatment purposes is referred to as "treatment light". The light-based epilation device and/or the light emission unit may comprise further light emission elements for emitting light that is not used as treatment light. E.g. the light emission unit may comprise at least one further light emission element for emitting light that is used to measure a skin parameter. Such light is referred to herein as "sensor light". The sensor light is reflected back from the skin and the reflection can be measured by a sensor that is adapted to measure a skin parameter such as skin color and/or hair color.

As was already explained, the controller of the light emission unit may be arranged to provide short interruptions (non-energizing gaps) of the energizing sequence that will be applied, i.e. 4 ms or below non-energizing gaps, during which the light emission unit will not emit treatment light. These non-energizing gaps can then be used to measure a skin parameter by emitting sensor light and using a sensor to analyze the reflected light. The short non-energizing gaps are chosen such that the user does not (in a statistical meaning) recognize the interruption(s) but recognizes the light emission as being continuous, i.e. without noticeable interruptions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

What is claimed is:

1. A method of cosmetic hair growth manipulation, comprising the steps of
providing a light-based epilation device for at least temporal hair removal comprising:
a light emission unit having a regular pattern array having rows and columns of light emission elements realized as semiconductor light emitter elements comprising LEDs, having at least two sub-groups of light emission elements, each of the sub-groups of light emission elements comprising at least one distinct light emission element, wherein the sub-groups of light emission elements are arranged for separate energizing; and
a controller unit arranged for energizing the sub-groups of light emission elements in accordance with an energizing sequence so that the light emission unit quasi-continuously emits treatment light, the energizing sequence comprising consecutive sub-sequences and where at least one sub-group is not energized at any given time instant, and where the energizing sequence comprises at least one non-energizing gap;

at least one sensor arranged for measuring a skin parameter during the non- energizing gap, wherein the at least one sensor is not influenced by light emitted by the light emission elements;

wherein the sub-groups of light emission elements are arranged as consecutive N times M sub-arrays of the array of light emission elements; and energizing in parallel at least two adjacent sub-groups of light emission elements for a first predefined time period while another sub-group of light emission elements adjacent to one of the energized sub-groups is not energized during a first subsequence of the energizing sequence, and then energizing in parallel at least one of the adjacent sub-groups of light emission elements energized during the first sub-sequence with the another sub-group of light emission elements for a second predefined time period while one of the sub-groups of light emission elements energized during the first sub-sequence is not energized during a second sub-sequence of the energizing sequence;

bringing a light output window of the light-based epilation device into contact with the skin of a human subject;

moving the light output window over the skin while maintaining skin contact and controlling the light-based epilation device to quasi-continuously emit light.

2. The method in accordance with claim 1, comprising the steps of providing the array of light emission elements in an oblong pattern and providing the sub-groups of light emission elements such that they are consecutively arranged in the longer elongation direction;

energizing adjacent sub-groups of the sub-groups of light emission elements from one end of the oblong array to the other end; and moving the output window perpendicular to the longer elongation direction at a speed at which a repeated energizing of the sub-groups leads to an essentially gap-free illumination on the skin.

3. The method in accordance with claim 1, comprising the steps of providing the array of light emission elements in an oblong pattern and providing the sub-groups of light emission elements such that they are consecutively arranged in the longer elongation direction;

energizing adjacent sub-groups of the sub-groups of light emission elements from one end of the oblong array to the other end;

measuring the speed of the movement;

controlling the energizing time periods in dependence on the determined speed in order to achieve an essentially gap-free illumination on the skin.

* * * * *